United States Patent [19]

Seltzer et al.

[11] Patent Number: 5,140,081

[45] Date of Patent: Aug. 18, 1992

[54] PEROXIDE FREE RADICAL INITIATORS CONTAINING HINDERED AMINE MOIETIES WITH LOW BASICITY

[75] Inventors: Raymond Seltzer, New City; Roland A. E. Winter, Armonk, both of N.Y.; Peter J. Schirmann, Fairfield, Conn.

[73] Assignee: Ciba-Geigy Corporation, Ardsley, N.Y.

[21] Appl. No.: 731,588

[22] Filed: Jul. 17, 1991

Related U.S. Application Data

[60] Division of Ser. No. 479,910, Feb. 14, 1990, Pat. No. 5,051,511, which is a continuation-in-part of Ser. No. 326,353, Mar. 21, 1989, abandoned.

[51] Int. Cl.$^5$ .............................. C08F 2/00; C08F 4/00
[52] U.S. Cl. .................................. 526/204; 525/375; 525/329.9; 525/123; 525/162
[58] Field of Search ............. 526/204; 525/375, 329.9, 525/123, 162

[56] References Cited

U.S. PATENT DOCUMENTS

| | | | |
|---|---|---|---|
| 3,956,269 | 5/1976 | Sheppard et al. | 260/192 |
| 4,042,773 | 8/1977 | Sheppard et al. | 526/208 |
| 4,045,426 | 8/1977 | Sheppard et al. | 260/174 |
| 4,045,427 | 8/1977 | Sheppard et al. | 260/192 |
| 4,055,714 | 10/1977 | Sheppard et al. | 526/208 |
| 4,129,586 | 12/1978 | Sheppard et al. | 260/465 |
| 4,344,876 | 8/1982 | Berner | 524/91 |
| 4,426,471 | 1/1984 | Berner | 524/91 |
| 4,426,472 | 1/1984 | Berner | 524/99 |
| 4,499,273 | 2/1985 | Fontana et al. | 546/188 |
| 4,822,883 | 4/1989 | Myers | 546/16 |

FOREIGN PATENT DOCUMENTS

| | | | |
|---|---|---|---|
| 56699 | 7/1982 | European Pat. Off. | |
| 233476 | 8/1987 | United Kingdom | 526/204 |

OTHER PUBLICATIONS

P. A. Callais, et al., Modern Paint & Coatings, 78, (9), 41 (1988).

Primary Examiner—Joseph L. Schofer
Assistant Examiner—Alex H. Walker
Attorney, Agent, or Firm—Luther A. R. Hall; JoAnn Villamizar

[57] ABSTRACT

Compounds which contain peroxide linkages as well as a hindered amine light stabilizer moiety of low basicity function as free radical polymerization initiators and provide a polymer containing a hindered amine stabilizer chemically bonded to said polymer. The low basicity of the instant compounds prevents interaction with acid catalysts used in some polymerization systems.

11 Claims, No Drawings

PEROXIDE FREE RADICAL INITIATORS CONTAINING HINDERED AMINE MOIETIES WITH LOW BASICITY

This is a divisional of Ser. No. 479,910 filed Feb. 14, 1990, now U.S. Pat. No. 5,051,511, which is a continuation-in-part of Ser. No. 326,353 filed Mar. 21, 1989, now abandoned.

The instant invention discloses hindered amine light stabilizers which combine low basicity with a peroxy group in the same molecule.

Copending patent application Ser. No. 326,850, now abandoned describes azo initiators containing hindered amine moieties with low basicity in the same molecule.

BACKGROUND OF THE INVENTION

The initiation of the polymerization of acrylic monomers with peroxy esters bearing hindered amine light stabilizing substituents is described by P. A. Callais et al in a paper presented in February 1988 at the "Waterborne and Higher Solids Coating Symposium" in New Orleans and published in Modern Paint and Coatings, 78 (9), 41 (1988).

Peroxides as free radical initiators containing hindered amine moieties is described in European Patent Application No. 233,476.

The combination of ultraviolet stabilizers (UV absorbers) with free radical initiating moieties (azo derivatives and peroxide compounds) are disclosed in U.S. Pat. Nos. 3,956,269; 4,042,773; 4,045,426; 4,045,427; 4,055,714 and 4,129,586.

The instant invention overcomes the drawbacks of the prior art materials which combine hindered amines with high basicity with peroxy groups.

The high basicity can neutralize acid catalysts that are commonly used in thermosetting resins thus causing cure inhibition. In other applications, the high basicity of many hindered amines can lead to undesired complexing and deactivation of metal ions which are used as catalysts for oxidative curing processes as well as undesired interactions with some pigment systems.

U.S. Pat. No. 4,822,883 describes peroxide free radical initiators containing hindered amine light stabilizer groups, but said hindered amines are not of low basicity.

THE INVENTION

The thermal cleavage of the peroxy moiety in the molecule results in the formation of free radicals which can be used to initiate free radical polymerization of ethylenically unsaturated monomers.

Another application involves the grafting of the stabilizer to existing substrates including a variety of polymers.

In either of these two situations, the instant light stabilizing hindered amine moiety becomes substantially chemically bonded to the substrate and becomes concomitantly resistant to migration, exudation, leaching, sublimation, volatilization or any process which is prone to remove an additive physically from the substrate it is supposed to protect.

More particularly, the instant invention pertains to a compound which is a free radical initiator which also contains a hindered amine light stabilizing moiety having low basicity, which compound has the formula I

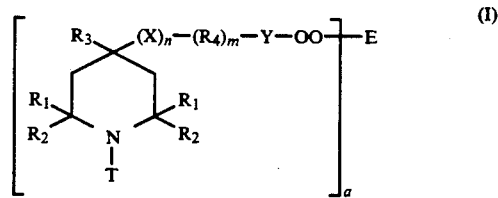

a is 1 or 2, n and m are independently 0 and 1, $R_1$ and $R_2$ are independently alkyl of 1 to 4 carbon atoms, or $R_1$ and $R_2$ together are pentamethylene, $R_3$ is hydrogen, alkyl of 1 to 8 carbon atoms, alkenyl of 2 to 8 carbon atoms, alkynyl of 2 to 8 carbon atoms, cycloalkyl of 5 to 6 carbon atoms, alkoxy of 1 to 8 carbon atoms, alkoxycarbonyl of 2 to 7 carbon atoms, aryl of 6 to 10 carbon atoms, aralkyl of 7 to 15 carbon atoms, alkanoyl of 1 to 8 carbon atoms, aroyl of 7 to 16 carbon atoms, alkanoyloxy of 1 to 7 carbon atoms, or aroyloxy of 6 to 10 carbon atoms, or $R_3$ together with $R_4$ form a cyclic structure of 5 to 7 atoms, X is —O—, —S—, —NG—, —CO—, —SO—, —SO$_2$—, —OCO—, —OSO—, —OSO$_2$—, —NG—CO—, —NHCONH— or —OCO—O— where G is hydrogen, alkyl of 1 to 8 carbon atoms, alkenyl of 2 to 8 carbon atoms, alkynyl of 2 to 8 carbon atoms, cycloalkyl of 5 to 6 carbon atoms, aryl of 6 to 10 carbon atoms, alkanoyl of 1 to 8 carbon atoms or G and $R_4$ together form a cyclic structure of 5 to 7 carbon atoms, $R_4$ is a diradical which is alkylene of 1 to 20 carbon atoms, arylene of 6 to 10 carbon atoms, cycloalkylene of 3 to 10 carbon atoms, aralkylene of 7 to 20 carbon atoms, alkynylene of 2 to 10 carbon atoms, alkadiynylene of 4 to 10 carbon atoms, alkenylene of 3 to 11 carbon atoms, alkadienylene of 5 to 11 carbon atoms, or said diradical interrupted by one or more oxygen, sulfur or nitrogen atoms, .

Y is —CO—, —SO$_2$—, —CR$_5$R$_6$—, —OCOE—, —NG—CO—E— or —OCO—CO, where $R_5$ and $R_6$ are independently alkyl of 1 to 10 carbon atoms, aryl of 6 to 10 carbon atoms, alkynyl of 2 to 10 carbon atoms, alkenyl of 2 to 8 carbon atoms or cycloalkyl of 5 to 6 carbon atoms, or $R_5$ and $R_6$ together are alkylene of 4 to 9 carbon atoms, and when E is tert-alkyl, tert-cycloalkyl or tert-aralkyl, $R_6$ is also —O—O—E, E, when a is 1, is hydrogen, alkanoyl of 2 to 20 carbon atoms, aroyl of 7 to 20 carbon atoms, tert-alkyl of 4 to 12 carbon atoms, tert-cycloalkyl of 4 to 12 carbon atoms, tert-aralkyl of 9 to 15 carbon atoms, alkoxycarbonyl of 2 to 20 carbon atoms, carbamoyl, phenylcarbamoyl, alkylcarbamoyl of 2 to 13 carbon atoms, cycloalkylcarbamoyl of 4 to 13 carbon atoms, alpha-hydroxyalkyl of 2 to 10 carbon atoms, alpha-hydroxycycloalkyl of 3 to 10 carbon atoms, alkylsulfonyl of 4 to 20 carbon atoms, cycloalkylsulfonyl of 3 to 12 carbon atoms, tert-alkoxyalkyl of 4 to 20 carbon atoms, tert-alkoxycycloalkyl of 4 to 20 carbon atoms, monovalent organometal, or the radical of formula II

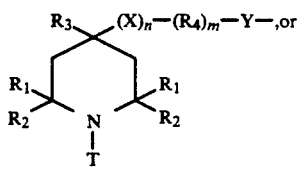

(II)

E, when a is 2, is di-tert-alkylene of 7 to 15 carbon atoms, di-tert-alkenylene of 8 to 16 carbon atoms, di-tert-alkynylene of 8 to 16 carbon atoms, di-tert-aralkylene of 12 to 20 carbon atoms, alkanedioyl of 3 to 12 carbon atoms, aryldicarbonyl of 8 to 16 carbon atoms or aralkyldicarbonyl of 9 to 18 carbon atoms, and T is formyl, —O—$T_1$, or —OCO—$T_2$, where $T_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl, and $T_2$ is alkyl of 1 to 18 carbon atoms, alkoxy of 1 to 18 carbon atoms, phenyl or said phenyl substituted by hydroxy, alkyl or alkoxy; or amino or said amino mono- or disubstituted by alkyl or phenyl.

Preferably $R_1$ and $R_2$ are each methyl.

$R_3$ is preferably hydrogen, alkyl of 1 to 4 carbon atoms, alkoxycarbonyl of 2 to 5 carbon atoms, alkanoyloxy of 1 to 4 carbon atoms, phenyl or alkoxy of 1 to 3 carbon atoms.

X is preferably —O—, —S—, —NG—, —O-CO—O—, —NGCOO—, —OCO— or —CO—.

$R_4$ is preferably alkylene of 1 to 8 carbon atoms, arylene of 6 to 10 carbon atoms, aralkylene of 8 to 16 carbon atoms or cycloalkylene of 4 to 8 carbon atoms.

When a is 1, E is preferably alkanoyl of 2 to 10 carbon atoms, aroyl of 7 to 10 carbon atoms, tert-alkyl of 4 to 8 carbon atoms, tert-aralkyl of 9 to 16 carbon atoms or the radical of formula II.

When a is 2, E is preferably di-tert-alkylene of 8 to 12 carbon atoms, di-tert-aralkylene of 12 to 15 carbon atoms or alkanedioyl of 3 to 6 carbon atoms.

G is preferably hydrogen, alkyl of 1 to 4 carbon atoms, cyclohexyl or phenyl.

$R_5$ is preferably alkyl of 1 to 6 carbon atoms, aryl of 6 to 10 carbon atoms or cycloalkyl of 5 to 6 carbon atoms.

T is preferably formyl, —$OT_1$ or —$OCOT_2$ where $T_1$ is alkyl of 1 to 18 carbon atoms, alkenyl of 2 to 3 carbon atoms, propargyl, alpha-methylbenzyl or cyclohexyl, and $T_2$ is alkyl of 1 to 18 carbon atoms.

Most preferably $T_1$ is methyl, heptyl, octyl, nonyl or cyclohexyl.

Most preferably $T_2$ is alkyl of 1 to 12 carbon atoms.

Most preferably $R_3$ is hydrogen, alkyl of 1 to 4 carbon atoms or alkoxy of 1 to 3 carbon atoms.

X is most preferably —O—, —NG—, —OCO—O, —NG—COO— or —OCO—.

$R_4$ is most preferably alkylene of 1 to 6 carbon atoms, phenylene, aralkylene of 9 to 12 carbon atoms or cycloalkylene of 5 to 7 carbon atoms.

Y is most preferably —CO—, —$CR_5R_6$— or —OCO—.

When a is 1, E is most preferably alkanoyl of 2 to 10 carbon atoms, benzoyl, tert-alkyl of 4 to 6 carbon atoms, tert-aralkyl of 9 to 12 carbon atoms or a radical of formula II.

When a is 2, E is most preferably di-tert-alkylene of 8 to 10 carbon atoms, di-tert-aralkylene of 12 carbon atoms or alkanedioyl of 4 to 6 carbon atoms.

G is most preferably hydrogen or alkyl of 1 to 4 carbon atoms.

$R_5$ is most preferably alkyl of 1 to 4 carbon atoms, phenyl or cyclohexyl.

The instant invention also pertains to a process of preparing a homo- or copolymer containing a hindered amine light stabilizer moiety chemically bonded to the backbone of said polymer which process comprises polymerizing one or more ethylenically unsaturated monomer capable of being polymerized by free radicals in the presence of an effective initiating amount of a compound of formula I.

The instant compounds can be prepared by methods well known in the art as outlined in European Patent Application 233,476.

The intermediates used to make the instant compounds are generally items of commerce.

Unsaturated polyester resins that can be cured by the composition of this invention usually include an unsaturated polyester and one or more polymerizable monomers. The unsaturated polyesters are, for instance, obtained by esterifying at least one ethylenically unsaturated di- or polycarboxylic acid, anhydride, or acid halide, such as maleic acid, fumaric acid, glutaconic acid, itaconic acid, mesaconic acid, citraconic acid, allylmalonic acid, allylsuccinic acid, tetrahydrophthalic acid and others with saturated or unsaturated di- or polyols, such as ethylene glycol, diethylene glycol, triethylene glycol, 1,2- and 1,3-propanediols, 1,2-, 1,3- and, 1,4-butanediols, 2,2-dimethyl-1,3-propanediols, 2,2-dimethyl-1,3-propanediol, 2-hydroxymethyl-2-methyl-1,3-propanediol, 2-buten-1,4-diol, 2,2,4-trimethyl-1,3-pentanediol, glycerol, pentaerythritol, mannitol and others. Mixtures of such polyacids and/or mixtures of such polyalcohols may also be used. The unsaturated di- or polycarboxylic acids may be partially replaced by saturated polycarboxylic acids, such as adipic acid, succinic acid, sebacic acid, and others and/or by aromatic polycarboxylic acids, such as phthalic acid, trimellitic acid, pyromellitic acid, isophthalic acid, and terephthalic acid. The acids used may be substituted by groups such as halogen. Examples of such suitable halogenated acids are, for instance, tetrachlorophthalic acid, 5,6-dicarboxy-1,2, -3,4,7,7-hexachlorobicyclo[2.2.1]heptane, and others.

The other component of the unsaturated polyester resin, the polymerizable monomer or monomers, are preferably ethylenically unsaturated monomers, such as styrene, chlorostyrene, vinyltoluene, divinylbenzene, alpha-methylstyrene, diallyl maleate, diallyl phthalate, dibutyl fumarate, acrylonitrile, triallyl phosphate, triallyl cyanurate, methyl acrylate, methyl methacrylate, n-butyl methacrylate, ethyl acrylate, and others or mixtures thereof, which are copolymerizable with said polyesters.

A preferred unsaturated polyester resin contains as the polyester component the esterification product of 1,2-propylene glycol (a polyalcohol), maleic anhydride (an anhydride of an unsaturated polycarboxylic acid) and phthalic anhydride (an anhydride of an aromatic dicarboxylic acid) as well as the monomer component, styrene.

Other unsaturated polyester resins that are useful in the practice of this invention are unsaturated vinyl ester resins, consisting of a vinyl ester resin component and one or more polymerizable monomer components. The vinyl ester resin component can be made by reacting a chloroepoxide such as epichlorohydrin with appropriate amounts of a glycol such as bisphenol A (2,2-di-(4-hydroxyphenyl)-propane, in the presence of a base such as sodium hydroxide, to yield a condensation product having terminal epoxy groups derived from the epichlorohydrin. Subsequent reaction of the condensation product with polymerizable unsaturated carboxylic acids in the presence or absence of acidic or basic catalysts, results in the formation of a vinyl ester terminated resin component. Normally, styrene is added as the polymerizable monomer component to complete the preparation of the unsaturated vinyl ester resin.

Temperatures of about 20° to 200° C. and peroxide levels of about 0.05 to 5% or more by weight of curable unsaturated polyester resin are normally employed in the curing process. The unsaturated polyester resins described above can be filled with various materials such as sulfur, glass fibers, carbon blacks, silicas, metal silicates, clays, metal carbonates, antioxidants, heat and light stabilizers, sensitizers, dyes, pigments, accelerators, metal oxides such as zinc oxide, blowing agents, etc.

The hindered amine-peroxide compound of the present invention is useful as a free radical initiator system for the polymerization or copolymerization of an ethylenically unsaturated monomer or mixtures thereof at suitable temperatures and pressures. The compound is useful not only in conventional isothermal polymerization processes but also in processes in which two or more increasing temperature steps are employed or a continuous increase in temperature is employed. Ethylenically unsaturated monomers include: olefins such as ethylene, propylene, styrene, alpha-methyl styrene, chlorostyrene, vinyl benzyl chloride, vinyl toluene, vinyl pyridine, divinyl benzene; diolefins such as 1,3-butadiene, isoprene and chloroprene; vinyl esters such as vinyl acetate, vinyl propionate, vinyl laurate, vinyl benzoate or divinyl carbonate; unsaturated nitriles such as acrylonitrile and methacrylonitrile; acrylic acid, methacrylic acid and their esters and amides, such as methyl ethyl, n-butyl and 2-ethylhexyl acrylates and methacrylates and acrylamide and methacrylamide; maleic anhydride; maleimide and N-substituted derivatives thereof such as n-phenylmaleimide; maleic and fumaric acids and their esters; vinyl halo and vinylidene halo compounds such as vinyl chloride, vinyl fluoride, vinylidene chloride and vinylidene fluoride; perhalo olefins such as tetrafluoroethylene, hexafluoropropylene and chlorotrifluoroethylene; vinyl esters such as methyl vinyl ether, ethyl vinyl ether, n-butyl vinyl ether; allyl esters such as allyl acetate, allyl benzoate, diallyl phthalate, allyl ethyl carbonate, triallyl phosphate, triallyl cyanurate, diallyl fumarate, diallyl succinate, and diallyl carbonate; acrolein; methyl vinyl ketone; and mixtures thereof.

Temperatures of 30° to 250° C., preferably 40° to 200° C., and peroxide levels of 0.005 to 3%, preferably 0.01 to 1%, by weight, based on monomer, are normally employed in the conventional polymerization or in the increasing temperature polymerization processes. Polymerization can be carried out in solution where solvents such as toluene may be used. Bulk, solution, suspension, or emulsion polymerization processes may be employed. The hindered amine-peroxide composition of this invention may be employed in these vinyl polymerization processes alone or together with other peroxides and azo initiators.

The hindered amine-peroxide composition of this invention is also useful for producing high impact polymers such as high impact polystyrene by initiating grafting of a monomer onto the backbone of elastomers (rubbers) such as polybutadienes, styrene-butadiene-styrene triblock copolymers, ethylene-propylene-diene terpolymers, etc. This composition is also useful with lower amounts of the rubber to produce high impact resistant polymers having impact resistance comparable to high impact polymers produced with larger amounts of rubber and conventional initiator systems. The above described vinyl polymerization conditions and initiator levels and up to 15% by weight of rubber (based on monomer) may be used for producing high impact polymers.

The ethylenically unsaturated comonomers may also contain a UV-absorbing moiety such as a hydroxyphenyl substituted benzotriazole or s-triazine, a hydroxy substituted benzophenone, an oxanilide or alpha-cyanocinnamate or a hindered amine light stabilizer moiety. Examples of such ethylenically unsaturated UV-absorbers are described in a number of United States patents which are hereby incorporated into this application by reference.

Ethylenically unsaturated UV absorbers are described in a number of U.S. Patents. Acrylated benzotriazoles are described in U.S. Pat. Nos. 4,413,095; 4,716,234; 4,785,063 and 4,803,254. Acryloxyalkyl benzotriazoles are described in U.S. Pat. No. 4,260,768. Vinyl substituted benzotriazoles are described in U.S. Pat. No. 4,508,882. Ethylenically unsaturated benzotriazoles are described in U.S. Pat. No. 3,493,539. Acrylated benzophenones are described in U.S. Pat. No. 4,310,650.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

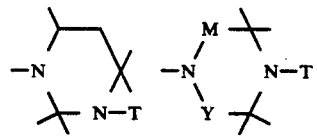

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA-or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins. 22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-α-(methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, β-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o-and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxy resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatability or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with aforementioned piperidine compounds are referenced in a paper by H. J. Heller in European Polymer Journal Supplement, 1969, pp 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-trizines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-$\beta,\beta$-diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alphacarbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alphadimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising (a) an acid catalyzed thermoset coating or enamel based on hot crosslinkable acrylic, polyester or alkyd resins, (b) a NT-substituted 2,2,6,6-tetraalkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbitol triphosphite, tetrakis-(2,4-di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1

1-Acetyl-2,2,6,6-tetramethyl-4-chlorocarbonyloxypiperidine Hydrochloride

A solution of 19.9 grams (0.1 mol) of 1-acetyl-2,2,6,6-tetramethyl-4-hydroxypiperidine in 150 ml of dry methyl ethyl ketone is added dropwise at 0° C. over a 30-minute period to a solution of 28 ml (approximately 0.4 mol) of phosgene in 150 ml of methyl ethyl ketone. The reaction mixture is stirred at 0° C. for one hour, then at 20° C. for eighteen hours. Excess dissolved phosgene is flushed out into an absorption trap with a stream of nitrogen. The solid precipitate is removed by filtration, washed twice with methyl ethyl ketone and dried with suction to yield 13.7 grams (52% yield) of the title compound which melts at 113°-114° C.

EXAMPLE 2

OO-tert-Amyl O-(1-Acetyl-2,2,6,6-tetramethylpiperidin-4-yl) Monoperoxycarbonate A solution of 4.2 grams of sodium hydroxide in 20 ml of water is cooled to 0° C., then 7.05 grams of tert-amyl hydroperoxide (85%) in 12.5 ml of toluene is added over 20 minutes followed by the portionwise addition of 13 grams (0.05 mol) of 1-acetyl-2,2,6,6-tetramethyl-4-chlorocarbonyloxypiperidine hydrochloride over a 30 minute period. The mixture is stirred at 0° C. for two hours, then at 20° C. for 18 hours. After cooling the reaction mixture to 0° C., the toluene layer is separated and washed with 25 ml of cold 2N sodium hydroxide solution, then with five 25 ml portions of water. The toluene solution is dried over anhydrous magnesium sulfate and stripped of solvent. The residue crystallized on standing and is then triturated with 10 ml of hexane, cooled and filtered to yield 10.7 grams (69% yield) of the title compound which melts at 70°–73° C.

Analysis: Calcd for $C_{17}H_{31}NO_5$: C, 62.0; H, 9.5; N, 4.3. Found: C, 62.4; H, 9.8; N, 4.2.

EXAMPLE 3

1-Cyclohexyloxy-2,2,6,6-tetramethyl-4-chlorocarbonyloxypiperidine Hydrochloride Following the procedure of Example 1, 1-cyclohexyloxy-2,2,6,6-tetramethyl-4-hydroxypiperidine is reacted with phosgene to form the title compound in a yield of 80%. The product melts at 174°–175° C.

Analysis: Calcd for $C_{16}H_{29}C_{12}NO_3$: C, 54.2; H, 8.2; N, 3.9. Found: C, 54.4; H, 8.1; N, 3.8.

EXAMPLE 4

OO-tert-Amyl O-(1-Cyclohexyloxy-2,2,6,6-tetramethylpiperidin-4-yl) Monoperoxycarbonate Following the procedure of Example 2, the intermediate prepared in Example 3 is transformed into the title compound. The product is purified by liquid chromatography to yield a viscous liquid in 52% yield.

EXAMPLES 5–8

A monomer composition comprising 25% butyl acrylate, 30% 2-hydroxyethyl acrylate, 27% butyl methacrylate, 15% styrene, and 3% acrylic acid is polymerized using different amounts of the peroxy initiator OO-tert-amyl O-(2-ethylhexyl) monoperoxycarbonate (TEAC Lupersol, Pennwalt). The various runs are carried out in refluxing xylene at 60% solids. Initiator concentrations are varied as a means of controlling polymer molecular weight.

To 100 grams of the monomer mixture is added 5.2 grams of the initiator corresponding to 0.32% "active oxygen" per 100 grams of monomers. The mixture of monomers and initiator is then pumped with a metering pump at a uniform rate over 1 62 minutes into a stirred reactior which contains 66.7 grams of xylene maintained at 135° C. The resulting solution is stirred for an additional two hours at 135° C. to complete the polymerization.

The method described above is repeated using respectively 8.1; 7.3 and 6.5 parts of initiator per 100 parts of monomers.

The polymers prepared in Examples 5–8 are examined for molecular weight and Gardner viscosity values.

EXAMPLES 9–11

Using the procedure and the identical monomer mixture described in Examples 5–8 resins are prepared from peroxy initiators containing hindered amine moieties. For the 100 grams of monomer mixture, 6.5 grams of these three peroxy initiators are used respectively in Examples 9–11:

Example 9: OO-tert-amyl O-(1,2,2,6,6-pentamethylpiperidin-4-yl) monoperoxycarbonate Example 10: OO-tert-amyl O-(1-acetyl-2,2,6,6-tetramethyl-piperidin-4-yl) monoperoxycarbonate Example 11: OO-tert-amyl O-(1-cyclohexyloxy-2,2,6,6-tetramethylpiperidin-4-yl) monoperoxycarbonate Evaluation of the high-solids acrylic resin solutions of Examples 9–11 are essentially equivalent in molecular weight and Gardner viscosity values of the resin solutions made in Examples 5–8, particularly Example 8 using the same amount of initiator.

EXAMPLE 12

The stabilized acrylic polyol prepared in Examples 9–11 is blended with sufficient unstabilized acrylic polyol, made by the same procedure of Example 5, so that in the final acrylic-melamine formulation described below there is 1of the hindered amine acrylate present based on total resin solids.

The acrylic-melamine formulation comprises (all values are in parts by weight) 70 parts of acrylic polyol mixture as described above, 18 parts of melamine (Cymel 303, American Cyanamid), 0.51 part of sulfonic acid catalyst (Cycat 600, 70% DDBSA, American Cyanamid), 0.6 part of flow aid (FC 431 50% solids fluorocarbon, 3M) and 8.8 parts of methyl amyl ketone.

Thermoset acrylic enamels are prepared using the formulations cited above.

Pieces of steel sheeting 4 in.×12 in. (9.16 cm×30.48 cm), coated with a polyester/epoxy primer, are then coated with a silver metallic base coat and finally with a clear finishing enamel. The basecoat is sprayed onto the coated sheet to a thickness of about 0.9 mil (0.023 mm) and air dried for three minutes.

The clear finishing enamel is then sprayed onto the sheet to a thickness of about 2 mils (0.05 mm). After air drying for ten minutes, the coated sheets are baked for thirty minutes at 250° F. (121° C.). The Knoop hardness values of the baked coating is then determined.

| Knoop Hardness of High Solid Acid Cured Coatings | |
|---|---|
| Light Stabilizer Present (1% by weight) | Knoop Hardness |
| Control | 9.3 |
| Copolymer of Example 11 | 9.1 |
| Copolymer of Example 11 plus 3% UV absorber* | 9.1 |
| Copolymer of Example 9 | 3.1 |

*2-(2-hydroxy-3,5-di-tert-amylphenyl)-2H-benzotriazole

The effectiveness of cure is assessed from the Knoop hardness values. The higher numbers indicate greater hardness and better cure. The instant compounds having the N-hydrocarbyl group do not cause cure retardation as do compounds such as those having N-alkyl substitution.

EXAMPLE 13

A thermoset acrylic enamel based on 70% by weight of a polyol composed of monomers such as 2-hydroxyethyl acrylate, butyl acrylate, butyl methacrylate, styrene, and acrylic acid and 30% by weight of a melamine resin in the presence of 0.6% dinonylnaphthalene disulfonic acid (based on total resin solids) is formulated to include either 1% by weight of hindered amine light stabilizers or 1% of a hindered amine light stabilizer and 3% of a benzotriazole UV absorber.

Commercially available epoxy primed 4"×12" (10.16 cm×30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoat to thickness of 1.7 mil (0.049 mm). After 15 minutes air drying, the coated panels are baked for 30 minutes at 250° F. (121° C.).

After storage for 1 week in an air-conditioned room, the coated panels are weathered in a QUV exposure apparatus according to ASTM G-53/77 using FS-40 bulbs.

| Acrylic Polymer | 20 Degree Gloss | | | | | | | | |
|---|---|---|---|---|---|---|---|---|---|
| | Hours QUV Exposure (FS-40) | | | | | | | | |
| | 0 | 925 | 1228 | 1500 | 1808 | 2419 | 3168 | 3476 | 4088 |
| Control | 93 | 86 | 88 | 82 | 57* | | | | |
| 1% Copolymer of Example 9 | 94 | 89 | 88 | 86 | 82 | 75 | 48* | | |
| 1% Copolymer of Example 11 | 93 | 89 | 91 | 86 | 85 | 67 | 54* | | |
| 1% Copolymer of Example 11 plus 3% Absorber** | 94 | 92 | 93 | 92 | 94 | 90 | 88 | 86 | 89 |

*indicates cracking
**2-(2-hydroxy-3,5-di-tert-amylphenyl)-2H-benzotriazole

EXAMPLE 14

A two component acrylic urethane refinish coating based on a polyol composed of monomers such as 2-hydroxyethyl acrylate, butyl acrylate, butyl methacrylate, styrene, and acrylic acid and an aliphatic isocyanate crosslinking resin (Desmodur N-3390 from Mobay Corp) in a 1.05/1.00 ratio is formulated to include 1% by weight of hindered amine light stabilizer.

Commercially available 4"×12" (10.16 cm×30.48 cm) steel panels (Advanced Coatings Technology) are first primed with a commercial epoxy primer and then spray coated with a thermoplastic silver metallic basecoat to a thickness of about 0.8 mil (0.023 mm) and air dried for 5 minutes. The stabilized acrylic urethane clearcoat is then sprayed onto the basecoat to thickness of 1.7 mil (0.049 mm). After storage for 1 month in an air-conditioned room, the coated panels are weathered in a QUV exposure apparatus according to ASTM G-53/77 using FS-40 bulbs.

| Acrylic Polymer | 20 Degree Gloss | | | |
|---|---|---|---|---|
| | QUV Exposure (FS-40) | | | |
| | 0 Hours | | 930 Hours | |
| | 20° Gloss | DOI* | 20 Gloss | DOI* |
| Control | 89 | 83 | 46 | 8 |
| Copolymer of | 88 | 78 | 75 | 60 |

| Acrylic Polymer | 20 Degree Gloss | | | |
|---|---|---|---|---|
| | QUV Exposure (FS-40) | | | |
| | 0 Hours | | 930 Hours | |
| | 20° Gloss | DOI* | 20 Gloss | DOI* |
| Example 11 | | | | |

*DOI is Distinctness of Image.

EXAMPLE 15

Light Stabilization of Polypropylene

This example illustrates the light stabilizing effectiveness of instant stabilizers.

Polypropylene powder (Himont Profax 6501) stabilized with 0.2% by weight of n-octadecyl 3,5-di-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi (1.2×10⁶ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

The time to failure for a polypropylene composition containing an instant compound as stabilizer is far longer than the time to failure for polypropylene having no such stabilizer present.

What is claimed is:

1. A composition stabilized against the deleterious effects of actinic light which comprises
   (a) a polymer, and
   (b) an effective stabilizing amount of a compound which is a free radical initiator which also contains a hindered amine light stabilizing moiety having low basicity, which compound has the formula I

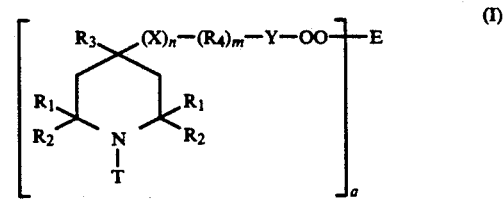

a is 1 or 2,
n and m are independently 0 and 1,
$R_1$ and $R_2$ are independently alkyl of 1 to 4 carbon atoms, or $R_1$ and $R_2$ together are pentamethylene,
$R_3$ is hydrogen, alkyl of 1 to 8 carbon atoms, alkenyl of 2 to 8 carbon atoms, alkynyl of 2 to 8 carbon atoms, cycloalkyl of 5 to 6 carbon atoms, alkoxy of 1 to 8 carbon atoms, alkoxycarbonyl of 2 to 7 carbon atoms, aryl of 6 to 10 carbon atoms, aralkyl of 7 to 15 carbon atoms, alkanoyl of 1 to 8 carbon atoms, aroyl of 7 to 16 carbon atoms, alkanoyloxy of 1 to 7 carbon atoms, or aroyloxy of 6 to 10 carbon atoms, or $R_3$ together with $R_4$ form a cyclic structure of 5 to 7 atoms, X is —O—, —S—, —NG—, —CO—, —SO—, —$SO_2$—, —OCO—, —OSO—, —$OSO_2$—, —N-G—CO—, —NHCONH— or —OCO—O— where G is hydrogen, alkyl of 1 to 8 carbon atoms, alkenyl of 2 to 8 carbon atoms, alkynyl of 2 to 8 carbon atoms, cycloalkyl of 5 to 6 carbon atoms, aryl of 6 to 10 carbon atoms, alkanoyl of 1 to 8 carbon atoms or G and $R_4$ together form a cyclic structure of 5 to 7 carbon atoms, $R_4$ is a diradical which is alkylene of 1 to 20 carbon atoms, arylene of 6 to 10 carbon atoms, cycloalkylene of 3 to 10 carbon atoms, aralkylene of 7 to 20 carbon atoms, alkynylene of 2 to 10 carbon atoms, alkadiynylene of 4 to 10 carbon atoms, alkenylene of 3 to 11 carbon atoms, alkadienylene of 5 to 11 carbon atoms, or said diradical interrupted by one or more oxygen, sulfur or nitrogen atoms, Y is —CO—, —$SO_2$—, —$CR_5R_6$—, —OCOE—, —NG—CO—E— or —OCO—CO, where $R_5$ and $R_6$ are independently alkyl of 1 to 10 carbon atoms, aryl of 6 to 10 carbon atoms, alkynyl of 2 to 10 carbon atoms, alkenyl of 2 to 8 carbon atoms or cycloalkyl of 5 to 6 carbon atoms, or $R_5$ and $R_6$ together are alkylene of 4 to 9 carbon atoms, and when E is tert-alkyl, tert-cycloalkyl or tert-aralkyl, $R_6$ is also —O—O—E, E, when a is 1, is hydrogen, alkanoyl of 2 to 20 carbon atoms, aroyl of 7 to 20 carbon atoms, tert-alkyl of 4 to 12 carbon atoms, tert-cycloalkyl of 4 to 12 carbon atoms, tert-aralkyl of 9 to 15 carbon atoms, alkoxycarbonyl of 2 to 20 carbon atoms, carbamoyl, phenylcarbamoyl, alkylcarbamoyl of 2 to 13 carbon atoms, cycloalkylcarbamoyl of 4 to 13 carbon atoms, alpha-hydroxyalkyl of 2 to 10 carbon atoms, alpha-hydroxycycloalkyl of 3 to 10 carbon atoms, alkylsulfonyl of 4 to 20 carbon atoms, cycloalkylsulfonyl of 3 to 12 carbon atoms, tert-alkoxyalkyl of 4 to 20 carbon atoms, tert-alkoxycycloalkyl of 4 to 20 carbon atoms, monovalent organometal, or the radical of formula II

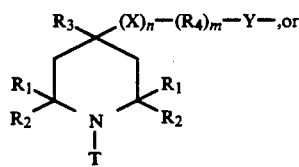

E, when a is 2, is di-tert-alkylene of 7 to 15 carbon atoms, di-tert-alkenylene of 8 to 16 carbon atoms, di-tert-alkynylene of 8 to 16 carbon atoms, di-tert-aralkylene of 12 to 20 carbon atoms, alkanedioyl of 3 to 12 carbon atoms, aryldicarbonyl of 8 to 16 carbon atoms or aralkyldicarbonyl of 9 to 18 carbon atoms, and T is formyl, —O—$T_1$ or —OCO—$T_2$, where $T_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl, and $T_2$ is alkyl of 1 to 18 carbon atoms, alkoxy of 1 to 18 carbon atoms, phenyl or said phenyl substituted by hydroxy, alkyl or alkoxy; or amino or said amino mono- or disubstituted by alkyl or phenyl.

2. A composition according to claim 1 wherein the polymer is a polyolefin.

3. A composition according to claim 2 wherein the polyolefin is polypropylene.

4. A composition according to claim 1 wherein the polymer is a coating system based on alkyd, acrylic, acrylic-alkyd, polyester, epoxide, urethane, polyamide, vinyl or epoxy-polyester resins.

5. A composition according to claim 1 which contains a UV absorber or additional light stabilizer.

6. A composition according to claim 1 wherein component (b) is 00-tert-amyl 0-(1-cyclohexyloxy-2,2,6,6-tetramethylpiperidin -4-yl) monoperoxycarbonate.

7. A composition according to claim 1 wherein component (b) is 00-tert-butyl 0-(1-octyloxy-2,2,6,6-tetramethylpiperidin-4-yl) monoperoxycarbonate.

8. A composition according to claim 1 wherein the polymer is an unsaturated elastomer which is polybutadiene, polyisoprene, styrene-butadiene copolymer or block copolymer, ethylene-propylene terpolymer, isoprene-isobutylene copolymer, acrylonitrile-butadiene copolymer, or styrene-isoprene copolymer or block copolymer.

9. A composition according to claim 8 wherein the elastomer is styrene-butadiene copolymer or block copolymer, styrene-isoprene copolymer or block copolymer or polybutadiene.

10. A composition according to claim 1 wherein component (a) is unsaturated and component (b) is grafted to component (a).

11. A method for stabilizing an organic material against oxidative, thermal or actinic degradation which comprises incorporating into said organic material an effective stabilizing amount of a compound which is a free radical initiator which also contains a hindered amine light stabilizing moiety having low basicity, which compound has the formula I

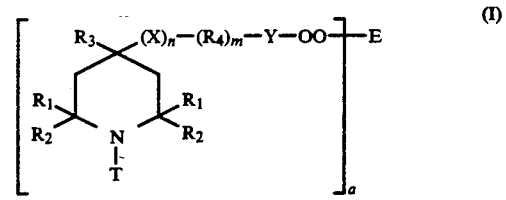

a is 1 or 2,
n and m are independently 0 and 1,
$R_1$ and $R_2$ are independently alkyl of 1 to 4 carbon atoms, or $R_1$ and $R_2$ together are pentamethylene,
$R_3$ is hydrogen, alkyl of 1 to 8 carbon atoms, alkenyl of 2 to 8 carbon atoms, alkynyl of 2 to 8 carbon atoms, cycloalkyl of 5 to 6 carbon atoms, alkoxy of 1 to 8 carbon atoms, alkoxycarbonyl of 2 to 7 carbon atoms, aryl of 6 to 10 carbon atoms, aralkyl of 7 to 15 carbon atoms, alkanoyl of 1 to 8 carbon atoms, aroyl of 7 to 16 carbon atoms, alkanoyloxy of 1 to 7 carbon atoms, or aroyloxy of 6 to 10 carbon atoms, or $R_3$ together with $R_4$ form a cyclic structure of 5 to 7 atoms, X is —O—, —S—, —NG—, —CO—, —SO—, —SO$_2$—, —OCO—, —OSO—, —OSO$_2$—, —N-G—CO—, —NHCONH— or —OCO—O— where G is hydrogen, alkyl of 1 to 8 carbon atoms, alkenyl of 2 to 8 carbon atoms, alkynyl of 2 to 8 carbon atoms, cycloalkyl of 5 to 6 carbon atoms, aryl of 6 to 10 carbon atoms, alkanoyl of 1 to 8 carbon atoms or G and $R_4$ together form a cyclic structure of 5 to 7 carbon atoms;

$R_4$ is a diradical which is alkylene of 1 to 20 carbon atoms, arylene of 6 to 10 carbon atoms, cycloalkylene of 3 to 10 carbon atoims, aralkylene of 7 to 20 carbon atoms, alkynylene of 2 to 10 carbon atoms, alkadiynylene of 4 to 10 carbon atoms, alkenylene of 3 to 11 carbon atoms, alkadienylene of 5 to 11 carbon atoms, or said diradical interrupted by one or more oxygen, sulfur or nitrogen atoms, Y is —CO—, —SO$_2$—, —CR$_5$R$_6$—, —OCOE—, —NG—CO—E— or —OCO—CO, where $R_5$ and $R_6$ are independently alkyl of 1 to 10 carbon atoms, aryl of 6 to 10 carbon atoms, alkynyl of 2 to 10 carbon atoms, alkenyl of 2 to 8 carbon atoms or cycloalkyl of 5 to 6 carbon atoms, or $R_5$ and $R_6$ together are alkylene of 4 to 9 carbon atoms, and when E is tert-alkyl, tert-cycloalkyl or tert-aralkyl, $R_6$ is also —O—O—E, E, when a is 1, is hydrogen, alkanoyl of 2 to 20 carbon atoms, aroyl of 7 to 20 carbon atoms, tert-alkyl of 4 to 12 carbon atoms, tert-cycloalkyl of 4 to 12 carbon atoms, tert-aralkyl of 9 to 15 carbon atoms, alkoxycarbonyl of 2 to 20 carbon atoms, carbamoyl, phenylcarbamoyl, alkylcarbamoyl of 2 to 13 carbon atoms, cycloalkylcarbamoyl of 4 to 13 carbon atoms, alpha-hydroxyalkyl of 2 to 10 carbon atoms, alpha-hydroxycycloalkyl of 3 to 10 carbon atoms, alkylsulfonyl of 4 to 20 carbon atoms, cycloalkylsulfonyl of 3 to 12 carbon atoms, tert-alkoxyalkyl of 4 to 20 carbon atoms, tert-alkoxycycloalkyl of 4 to 20 carbon atoms, monovalent organometal, or the radical of formula II

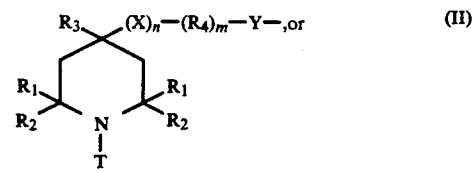

E, when a is 2, is di-tert-alkylene of 7 to 15 carbon atoms, di-tert-alkenylene of 8 to 16 carbon atoms, di-tert-alkynylene of 8 to 16 carbon atoms, di-tert-aralkylene of 12 to 20 carbon atoms, alkanedioyl of 3 to 12 carbon atoms, aryldicarbonyl of 8 to 16 carbon atoms or aralkyldicarbonyl of 9 to 18 carbon atoms, and T is formyl, —O—T$_1$ or —OCO—T$_2$, where T$_1$ is alkyl of 1 to 36 carbon atoms, alkenyl of 2 to 18 carbon atoms, alkynyl of 2 to 18 carbon atoms, aralkyl of 7 to 15 carbon atoms, cycloalkyl of 5 to 12 carbon atoms, cycloalkenyl of 5 to 12 carbon atoms, a radical of a saturated or unsaturated bicyclic or tricyclic hydrocarbon of 7 to 12 carbon atoms, or aryl of 6 to 10 carbon atoms or said aryl substituted by alkyl, and T$_2$ is alkyl of 1 to 18 carbon atoms, alkoxy of 1 to 18 carbon atoms, phenyl or said phenyl substituted by hydroxy, alkyl or alkoxy; or amino or said amino mono- or disubstituted by alkyl or phenyl.

* * * * *